United States Patent
Giffey et al.

(10) Patent No.: US 11,872,114 B2
(45) Date of Patent: Jan. 16, 2024

(54) METHOD AND APPARATUS FOR HIGH-SPEED CROSS-FOLDING OF ABSORBENT SANITARY PRODUCTS

(71) Applicant: Curt G. Joa, Inc., Sheboygan Falls, WI (US)

(72) Inventors: Zachary J. Giffey, Plymouth, WI (US); Scott A. Roehrborn, Sheboygan, WI (US)

(73) Assignee: CURT G. JOA, INC., Sheboygan Falls, WI (US)

( * ) Notice: Subject to any disclaimer, the term of this patent is extended or adjusted under 35 U.S.C. 154(b) by 183 days.

(21) Appl. No.: 16/728,445

(22) Filed: Dec. 27, 2019

(65) Prior Publication Data

US 2020/0237572 A1 Jul. 30, 2020

Related U.S. Application Data

(60) Provisional application No. 62/796,218, filed on Jan. 24, 2019.

(51) Int. Cl.
*A61F 13/15* (2006.01)
*B65G 15/62* (2006.01)
(Continued)

(52) U.S. Cl.
CPC .. *A61F 13/15747* (2013.01); *A61F 13/15764* (2013.01); *B65G 15/62* (2013.01);
(Continued)

(58) Field of Classification Search
CPC ................ A61F 13/15747; A61F 13/15; A61F 13/15764; B65G 15/62; B65G 17/46;
(Continued)

(56) References Cited

U.S. PATENT DOCUMENTS 1,913,001 A * 6/1933 Ross ..................... B67C 7/0006
198/803.11
2,358,292 A * 9/1944 Malhiot ................. B65G 17/26
198/803.11
(Continued)

FOREIGN PATENT DOCUMENTS

WO 2012123813 A1 9/2012

OTHER PUBLICATIONS

Supplementary European Search Report dated Sep. 21, 2017 regarding EP Application No. 14880017.0, 5 pages.
(Continued)

*Primary Examiner* — Robert F Long
*Assistant Examiner* — Eduardo R Ferrero
(74) *Attorney, Agent, or Firm* — Klintworth & Rozenblat IP LLP (57) ABSTRACT

A system and method for folding a discrete absorbent sanitary product includes conveying a product in a machine direction along a main conveyor, folding the product at a first folding station, and later folding the absorbent sanitary product at a second folding station. The product is folded at each of the first and second folding stations by engaging the product with a first drum and rotating the absorbent sanitary product in a first rotational direction, contacting the product with one or more folding fingers traveling in the machine direction, engaging the product with a rotating member adjacent to the first drum and downstream therefrom in the machine direction, the rotating member rotating in the first rotational direction, and folding the product over the one or more folding fingers via rotation of the rotating member in the first rotational direction.

21 Claims, 5 Drawing Sheets

(51) Int. Cl.
  *B65H 45/12* (2006.01)
  *B65G 17/46* (2006.01)
  *B65H 45/18* (2006.01)
  *B65H 45/16* (2006.01)
  *B65G 17/32* (2006.01)
  *B65G 15/58* (2006.01)

(52) U.S. Cl.
  CPC ............ *B65G 17/46* (2013.01); *B65H 45/12* (2013.01); *B65H 45/16* (2013.01); *B65H 45/18* (2013.01); *B65G 15/58* (2013.01); *B65G 17/323* (2013.01); *B65H 2404/2321* (2013.01); *B65H 2404/62* (2013.01)

(58) Field of Classification Search
  CPC .. B65G 17/323; B65G 21/2027; B65G 17/26; B65G 47/841; B65G 15/58; B65H 2801/57; B65H 2404/2321; B65H 2404/62; B65H 45/14; B65H 45/12; B65H 45/16; B65H 45/18; B65H 45/161; B65H 2404/232
  See application file for complete search history.

(56) References Cited

U.S. PATENT DOCUMENTS

| | | | | |
|---|---|---|---|---|
| 2,470,762 A * | 5/1949 | Dickenson | ............. | B65H 45/18 493/27 |
| 3,325,977 A * | 6/1967 | Kirsten | ................... | B65B 43/54 198/803.11 |
| 3,568,815 A * | 3/1971 | Wiseman | ........... | B65H 31/3063 198/607 |
| 3,572,689 A | 3/1971 | Murphy et al. | | |
| 3,578,311 A * | 5/1971 | Wood | ...................... | B65B 63/04 493/418 |
| 3,628,654 A * | 12/1971 | Haracz | ................... | B65G 17/46 198/689.1 |
| 3,682,469 A * | 8/1972 | Itoh | ...................... | B65G 17/323 271/12 |
| 3,747,917 A * | 7/1973 | Roda | ...................... | B65H 45/14 493/14 |
| 3,859,898 A * | 1/1975 | Besserdich | ............. | B31B 70/00 270/45 |
| 3,905,593 A * | 9/1975 | Behn | ...................... | B65H 45/18 493/441 |
| 3,941,233 A * | 3/1976 | Aiuola | ................... | B65G 47/843 198/803.5 |
| 3,998,447 A * | 12/1976 | Joa | ..................... | A61F 13/15747 493/938 |
| 4,157,058 A | 6/1979 | Vogel | | |
| 4,288,067 A * | 9/1981 | Vigano' | ................... | B65H 27/00 493/420 |
| 4,502,592 A * | 3/1985 | Ramcke | ................... | B65G 15/10 198/626.5 |
| 4,504,259 A * | 3/1985 | Lindenmuller | ........ | B65H 45/12 493/917 |
| 4,508,528 A | 4/1985 | Hirsch et al. | | |
| 4,549,876 A | 10/1985 | Baker et al. | | |
| 4,556,146 A * | 12/1985 | Swanson | ................... | A61F 15/001 206/438 |
| 4,560,060 A * | 12/1985 | Lenhart | ................... | F02P 9/007 198/453 |
| 4,589,541 A * | 5/1986 | Lisec | ................... | B65G 49/063 198/468.4 |
| 4,616,815 A | 10/1986 | Vijuk | | |
| 4,717,375 A | 1/1988 | Lundmark | | |
| 4,938,739 A | 7/1990 | Nilsson | | |
| 5,074,547 A | 12/1991 | Smith et al. | | |
| 5,152,734 A | 10/1992 | McAdam, III et al. | | |
| 5,337,887 A * | 8/1994 | Greenwell | ............. | B65G 17/26 198/867.14 |
| 5,478,336 A * | 12/1995 | Pigneul | ................... | A61F 13/5514 206/438 |
| 5,634,875 A * | 6/1997 | Fisk | ...................... | B65H 45/12 493/422 |
| 5,651,313 A * | 7/1997 | Kowalewski | .......... | B65H 5/224 101/232 |
| 5,687,641 A * | 11/1997 | Williamson | ........... | A21C 3/022 198/689.1 |
| 5,788,805 A | 8/1998 | Herrmann | | |
| 5,795,433 A | 8/1998 | Niedermeyer | | |
| 5,954,201 A * | 9/1999 | Finch | ................... | A61F 13/5514 206/440 |
| 6,015,934 A * | 1/2000 | Lee | ........................ | B65H 39/14 604/358 |
| 6,074,376 A * | 6/2000 | Mills | ...................... | A61B 17/06 206/438 |
| 6,086,522 A | 7/2000 | Hechler | | |
| 6,158,573 A * | 12/2000 | Janzen | ................... | B65G 15/58 198/689.1 |
| 6,514,187 B2 | 2/2003 | Coenen et al. | | |
| 7,004,309 B2 * | 2/2006 | Sherwood | .............. | B65G 15/58 198/689.1 |
| 7,264,583 B2 | 9/2007 | Gelli et al. | | |
| 7,377,378 B2 * | 5/2008 | Cash, III | ................ | B65G 17/26 198/803.11 |
| 7,384,386 B2 | 6/2008 | Sosalla | | |
| 7,399,266 B2 | 7/2008 | Aiolfi et al. | | |
| 7,722,027 B2 * | 5/2010 | Gibson | ................... | B65G 15/58 271/12 |
| 8,257,237 B2 | 9/2012 | Burns, Jr. et al. | | |
| 8,439,814 B2 | 5/2013 | Piantoni et al. | | |
| 8,485,956 B2 | 7/2013 | Burns, Jr. et al. | | |
| 8,617,040 B2 | 12/2013 | Coenen et al. | | |
| 8,870,732 B2 | 10/2014 | Schneider et al. | | |
| 2001/0052449 A1* | 12/2001 | Emery | ................... | B65G 15/58 198/689.1 |
| 2002/0112939 A1* | 8/2002 | Sumi | ..................... | B65G 47/848 198/377.08 |
| 2003/0019729 A1* | 1/2003 | Janzen | ................... | B65G 15/58 198/689.1 |
| 2003/0114814 A1* | 6/2003 | Baker | ................... | A61F 13/491 604/378 |
| 2004/0063559 A1 | 4/2004 | Ochsenbauer | | |
| 2005/0092440 A1 | 5/2005 | Lindsay et al. | | |
| 2006/0276320 A1 | 12/2006 | Aiolfi et al. | | |
| 2007/0129230 A1 | 6/2007 | Sosalla | | |
| 2008/0026925 A1 | 1/2008 | Allen et al. | | |
| 2008/0083203 A1* | 4/2008 | Bich | ..................... | A01D 75/182 56/14.4 |
| 2010/0251683 A1* | 10/2010 | Thompson | ........... | A01D 75/182 56/14.4 |
| 2011/0003673 A1 | 1/2011 | Piantoni et al. | | |
| 2011/0203431 A1* | 8/2011 | Cocozzella | ........... | B26D 11/00 83/23 |
| 2011/0251040 A1 | 10/2011 | Yamamoto et al. | | |
| 2012/0088646 A1* | 4/2012 | Berggren | ......... | A61F 13/15747 493/393 |
| 2012/0157288 A1 | 6/2012 | Coenen et al. | | |
| 2012/0302418 A1 | 11/2012 | Burns, Jr. et al. | | |
| 2013/0036887 A1* | 2/2013 | Moore | ..................... | B26D 7/32 198/470.1 |
| 2013/0130881 A1* | 5/2013 | Pastrello | ........... | A61F 13/55135 493/405 |
| 2013/0270065 A1 | 10/2013 | Papsdorf et al. | | |
| 2013/0296152 A1* | 11/2013 | Murakami | ........ | A61F 13/15747 493/405 |
| 2014/0171284 A1 | 6/2014 | Coenen et al. | | |
| 2014/0178168 A1* | 6/2014 | Wang | ................... | B65G 47/907 414/749.6 |
| 2015/0202092 A1* | 7/2015 | McCabe | ........... | A61F 13/15747 493/416 |
| 2015/0336378 A1* | 11/2015 | Guttmann | ............ | B65H 3/0816 101/483 |
| 2015/0374555 A1* | 12/2015 | Chen | ............... | A61F 13/15747 493/427 |
| 2016/0096685 A1* | 4/2016 | Sherwood | .............. | B65G 21/22 198/678.1 |
| 2016/0194174 A1 | 7/2016 | Schoulz | | |

(56) References Cited

U.S. PATENT DOCUMENTS

2016/0213524 A1\* 7/2016 Davidson .......... A61F 13/15764
2016/0228303 A1\* 8/2016 Wada ................ A61F 13/15747
2020/0335374 A1\* 10/2020 Liao ........................ H01L 24/74

OTHER PUBLICATIONS

Extended European Search Report dated Jun. 24, 2019 regarding EP Application No. 18215765.1, 11 pages.

\* cited by examiner

METHOD AND APPARATUS FOR HIGH-SPEED CROSS-FOLDING OF ABSORBENT SANITARY PRODUCTS

CROSS-REFERENCE TO RELATED APPLICATIONS

The present invention claims priority to U.S. Provisional Patent Application Ser. No. 62/796,218 filed Jan. 24, 2019, the disclosure of which is incorporated herein by reference in its entirety.

BACKGROUND OF THE INVENTION

Embodiments of the invention relate generally to absorbent sanitary products or articles and, more particularly, to methods and apparatuses for high-speed cross-folding of absorbent sanitary products.

Absorbent sanitary products, such as disposable diapers, feminine hygiene articles, adult incontinent articles, and other absorbent articles, typically comprise an absorbent insert or patch that is positioned proximate a wearer's body when worn. In such articles, a chassis may be provided that supports and holds the insert in place, along with other various patches, reusable fasteners, and the like.

It is recognized that most absorbent sanitary products require some type of folding during production. In the diaper industry, for example, diapers are normally folded by feeding a succession of flat diapers along a linear conveyor, arresting each flat diaper with a central portion positioned over a transverse opening in the linear conveyor, and folding the diaper into a U by inserting a folding member through the opening. For infant diapers, only a single cross-fold is made generally at a crotch region to reduce the length of the diapers prior to packaging. For adult incontinent articles, a second cross-fold is often made to further reduce a length of the articles prior to packaging, with the second cross-fold performed in such a manner and in a location that results in the articles having four stacked layers of material in its final folded state.

For feminine hygiene articles, it is recognized that the typical folding pattern utilized for these articles is different from those utilized for infant diapers and adult incontinent articles. That is, feminine hygiene articles are often folded in a manner that results in the article having three stacked layers of material in its final folded state. Accordingly, existing methods and apparatuses for performing the folding of these articles may not be sufficient and/or useable for folding feminine hygiene articles.

Accordingly, there exists need for an apparatus and method for performing high-speed cross-folding of feminine hygiene articles that will provide a desired folding pattern in the article. It is desirable for such an apparatus and method to be incorporated into existing product manufacturing lines, without major modifications to the lines having to be made.

BRIEF DESCRIPTION OF THE INVENTION

In accordance with one aspect of the invention, a method for folding discrete absorbent sanitary products includes conveying an absorbent sanitary product in a machine direction along an inverted main conveyor and performing a first folding of the absorbent sanitary product at a first folding station, the first folding being performed at a first folding point of the absorbent sanitary product located between a leading edge and a midsection of the absorbent sanitary product. The method also includes performing a second folding of the absorbent sanitary product at a second folding station, the second folding being performed at a second folding point of the absorbent sanitary product located between a trailing edge and a midsection of the absorbent sanitary product. In performing each of the first folding and the second folding at the first folding station and the second folding station, respectively, the method further includes engaging the absorbent sanitary product with a first drum and rotating the absorbent sanitary product in a first rotational direction, contacting the absorbent sanitary product with one or more folding fingers traveling in the machine direction, engaging the absorbent sanitary product with a second drum adjacent to the first drum and downstream therefrom in the machine direction, the second drum rotating in the first rotational direction, and folding the absorbent sanitary product over the one or more folding fingers via rotation of the second drum in the first rotational direction.

In accordance with another aspect of the invention, a folding system for folding a plurality of discrete absorbent sanitary products includes an inverted main conveyor configured to convey absorbent sanitary products thereon in a machine direction, the absorbent sanitary products being maintained on the main conveyor via a vacuum, a first folding station positioned to receive the absorbent sanitary products on the main conveyor and controlled to perform a first folding thereof at a first folding point between a leading edge and a midsection of the absorbent sanitary product, and a second folding station positioned downstream from the first folding station in the machine direction to receive the absorbent sanitary products on the main conveyor after the first folding thereof, the second folding station controlled to perform a second folding thereof at a second folding point between a trailing edge and a midsection of the absorbent sanitary product. Each of the first folding station and the second folding station further includes a first drum rotating in the machine direction to engage an absorbent sanitary product and cause the leading edge of the absorbent sanitary product to rotate away from the main conveyor, a second drum positioned adjacent the first drum and downstream in the machine direction, the second drum rotating in the machine direction to engage the absorbent sanitary product and cause the absorbent sanitary product to rotate back toward the main conveyor, and one or more guide transporters each comprising a plurality of folding fingers, with each of the one or more guide transporters configured to translate a folding finger of the plurality of folding fingers in the machine direction at a same speed as the main conveyor and position the folding finger to contact the absorbent sanitary product. The absorbent sanitary product is folded over the folding finger as the second drum causes the absorbent sanitary product to rotate back toward the main conveyor.

In accordance with yet another aspect of the invention, a method of assembling a folding system includes providing an inverted main conveyor configured to convey absorbent sanitary products thereon in a machine direction, the absorbent sanitary products being maintained on the main conveyor via a vacuum, positioning a first folding station at a first location on the main conveyor to receive the absorbent sanitary products, the first folding station controlled to perform a first folding thereof at a first folding point between a leading edge and a midsection of the absorbent sanitary product, and positioning a second folding station at a second location on the main conveyor downstream from the first location to receive the absorbent sanitary products after the first folding thereof, the second folding station controlled to perform a second folding thereof at a second folding point between a trailing edge and a midsection of the absorbent sanitary product. In positioning each of the first folding station and the second folding station, the method further includes providing a first drum that rotates in the machine direction to engage an absorbent sanitary product and cause the leading edge of the absorbent sanitary product to rotate away from the main conveyor, providing a second drum positioned adjacent the first drum and downstream in the machine direction that rotates in the machine direction to engage the absorbent sanitary product and cause the absorbent sanitary product to rotate back toward the main conveyor, and providing one or more guide transporters that each comprises a plurality of folding fingers, with each of the one or more guide transporters configured to translate a folding finger of the plurality of folding fingers in the machine direction at a same speed as the main conveyor and position the folding finger to contact the absorbent sanitary product, so as to provide for folding of the absorbent sanitary product over the folding finger as the second drum causes the absorbent sanitary product to rotate back toward the main conveyor.

These and other advantages and features will be more readily understood from the following detailed description of preferred embodiments of the invention that is provided in connection with the accompanying drawings.

BRIEF DESCRIPTION OF THE DRAWINGS

The drawings illustrate embodiments presently contemplated for carrying out the invention.

In the drawings.

DETAILED DESCRIPTION

Embodiments of the present invention provide for a method and apparatus for high-speed cross-folding of an absorbent sanitary product such as a feminine hygiene article.

While the method and apparatus of the present invention will be described herein with reference to folding a feminine hygiene article, it is recognized that the method and apparatus are also suitable for folding other articles, such as sanitary napkins or other absorbent sanitary products. A continuous web of articles, such as feminine hygiene articles, may be constructed, severed and separated into discrete units on a manufacturing line. The discrete articles may then be presented to an apparatus, such as one or more folders, to be manipulated and prepared for packaging.

Figure 1:
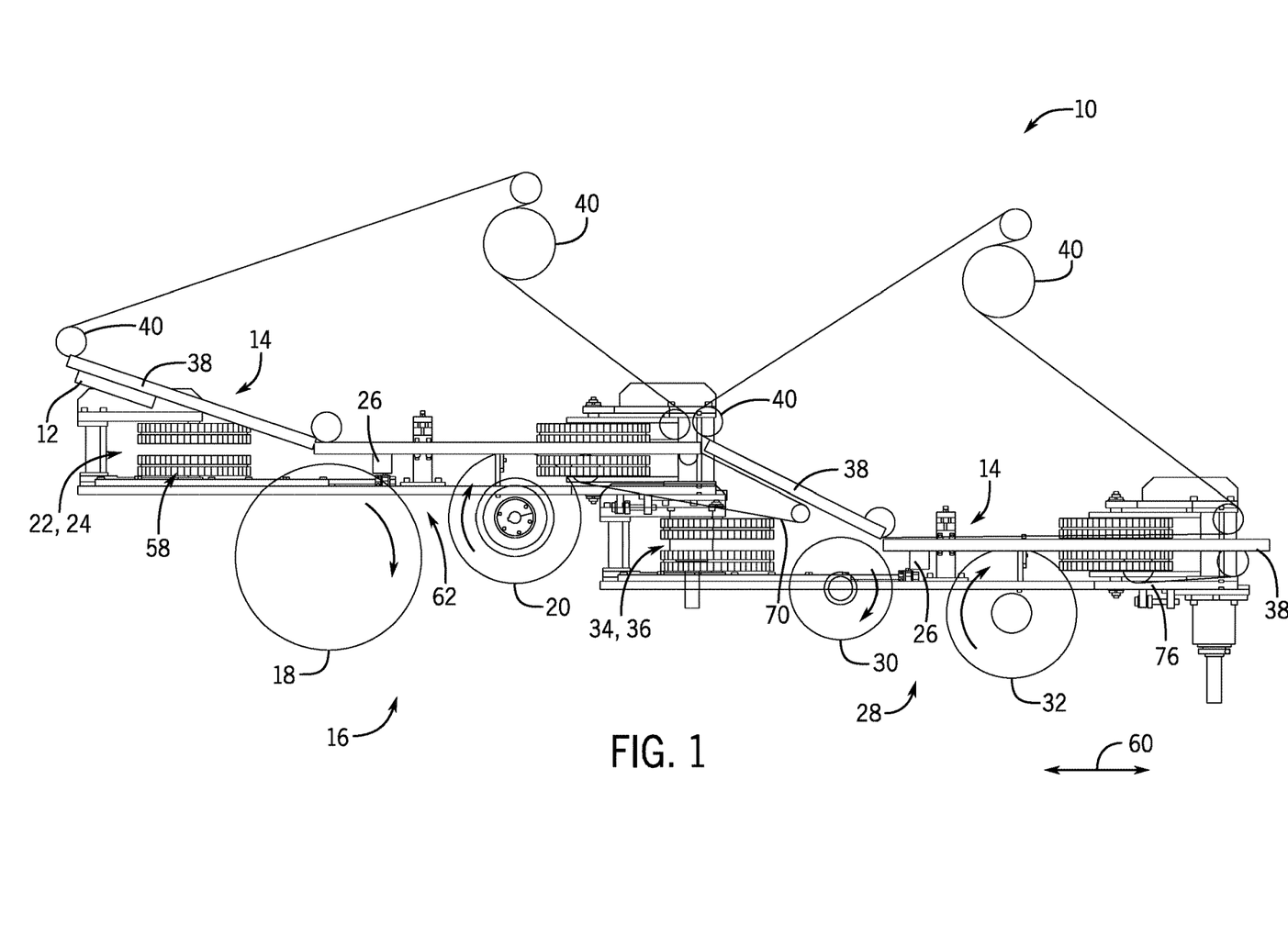
FIG. 1 is a schematic side view of a folding system for performing high-speed cross-folding of absorbent sanitary products or articles, according to an embodiment of the invention.

Various views of a folding system 10 of the present invention and an article 12 folded thereby are shown in FIGS. 1-6 according to an embodiment of the invention. Discrete articles 12 to be folded, such as feminine hygiene articles, are fed into the folding system 10 for folding, with such articles 12 being provided from an incoming web of material that is severed into discrete articles via, for example, a rotary die and anvil (not shown) and then transferred to the folding system 10. As generally shown in FIG. 1, the articles 12 are conveyed to folding system 10 via a main conveyor 14 and fed to a first folding station or zone 16 comprising a combination of drums 18, 20 which control movement and initiate a first cross-wise folding, as will be described later. At the first folding station 16, one or more guide transporters 22, 24 rotate folding guides or fingers 26 to enable the first cross-wise folding, with the folding fingers 26 tucking the article 12 to support the folded article 12. The folded articles 12 are then passed downstream via main conveyor 14 to a second folding station 28 comprising a combination of drums 30, 32 which control movement and initiate a second cross-wise folding, as will be described later. At the second folding station 28, one or more guide transporters 34, 36 rotate a plurality of folding guides or fingers 26 to enable the second cross-wise folding, with the folding fingers tucking the article 12 to support the folded article.

As shown in FIG. 1, according to an exemplary embodiment, main conveyor 14 is configured as an inverted conveyor comprising a belt 38 that is driven via a plurality of motor-driven rollers 40. The inverted main conveyor 14 holds articles 12 in place thereon via a vacuum suction and is connected to a source of vacuum (not shown) that creates such a vacuum along the length of the main conveyor 14 in order to hold the articles 12 in place and transport them along the conveyor. The articles 12 may be positioned/oriented on main conveyor 14 such that an absorbent insert or patch 41 (FIG. 5) thereof is in a "pad down" position, with the absorbent insert facing away from main conveyor 14. Also, according to an exemplary embodiment and as shown in FIG. 1, portions of main conveyor 14 may be oriented at a decline so as to assist folding fingers 26 in engaging the article 12 while it is moving on the conveyor. In particular, portions of main conveyor 14 immediately proximate each of first folding station 16 and second folding station 28 may be declined so as to be oriented at a descending or downward angle in order for articles 12 to better engage the forward positioned or first drum 18, 30 in each of the first and second folding stations 16, 28.

While main conveyor 14 is illustrated in FIG. 1 as an inverted conveyor, it is recognized that main conveyor 14 could be provided as a conventional conveyor that is positioned below articles 12 and provides support thereto with or without the need for a vacuum. In such an embodiment, the articles 12 may be positioned/oriented on main conveyor 14 such that absorbent insert is in a "pad up" position, with the absorbent insert facing away from main conveyor 14.

Figure 3:
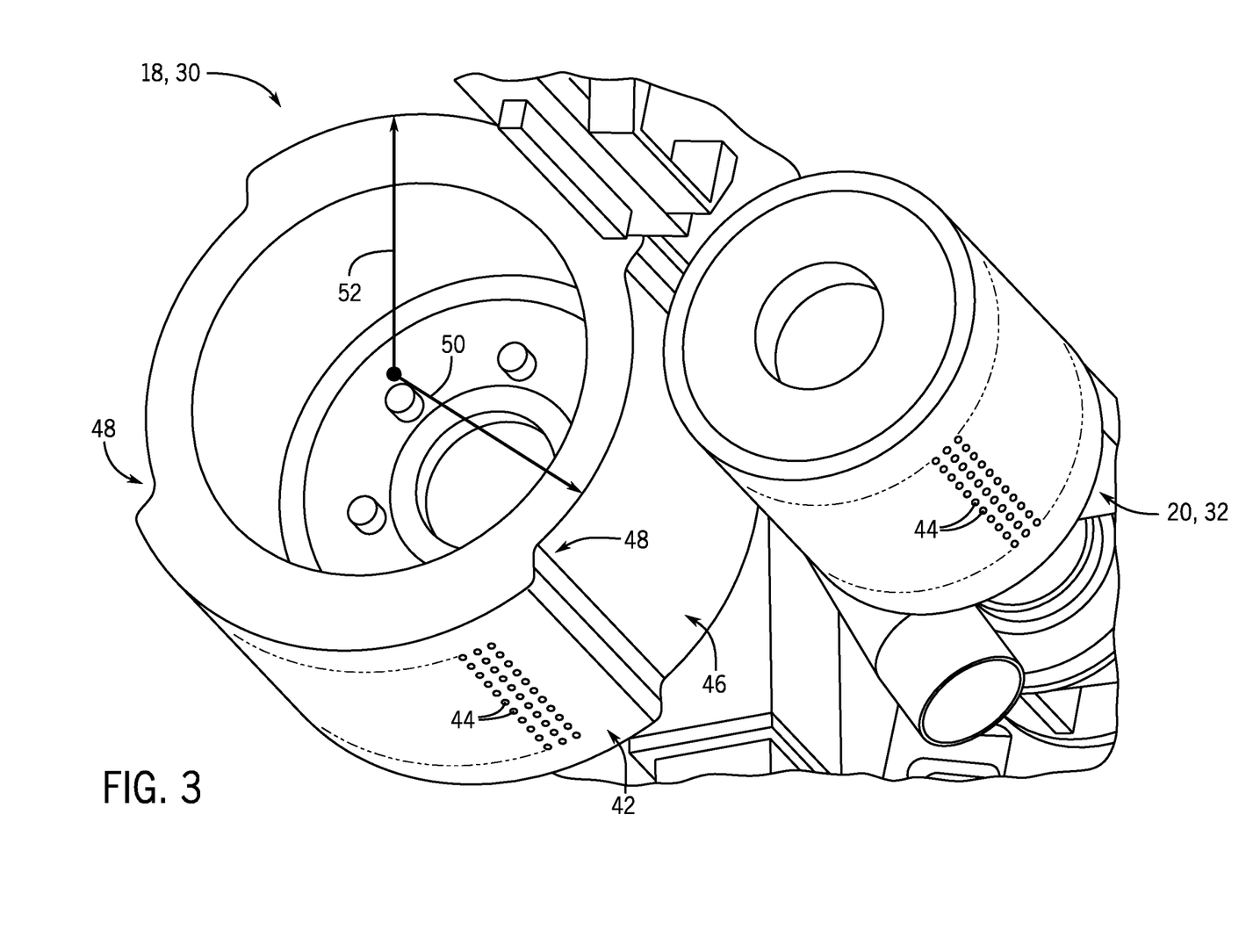
FIG. 3 is a detailed perspective view of first and second drums included in folding stations of the folding system of FIG. 1, according to an embodiment of the invention.

In operation, the main conveyor 14 carries an article 12 to first folding station 16, where main conveyor 14 interacts with first vacuum drum 18 that rotates/operates clockwise as shown in the view of FIG. 1 to transport the article 12. As best shown in FIG. 3, first vacuum drum 18 includes one or more article retaining portions or "vacuum portions" 42 on its outer surface in order to hold (when desired) and control the path of the articles 12. The vacuum portion(s) 42 are formed with a plurality of vacuum holes or ports 44 on the surface. A vacuum slot (not shown) is provided on an end face surface (commutating surface) of the first vacuum drum 18 and is adapted to put the plurality of vacuum ports 44 in communication with a vacuum source (not shown).

According to an exemplary embodiment, the one or more vacuum portions 42 are formed to jut outwardly from a remaining non-vacuum portion 46 of the drum 18—with this remaining non-vacuum portion 46 not having vacuum ports formed therein. According to one embodiment, two vacuum portions 42 are formed on drum 18, but it is recognized that more or less vacuum portions 42 may be provided on first vacuum drum 18, with it being recognized that the number of vacuum portions 42 may be based (at least on part) on a size of the drum 18. At transitions between the vacuum portion(s) 42 and the non-vacuum portion 46, notches 48 are formed in the drum 18 where the drum increases from a first radius 50 (of the non-vacuum portion 46) to a second radius 52 (of vacuum portion(s) 42). Positioning of folding fingers 26 may be controlled so as to align them with these notches 48 on drum 18 to accommodate folding of the articles 12, as will be explained further below.

Figure 2:
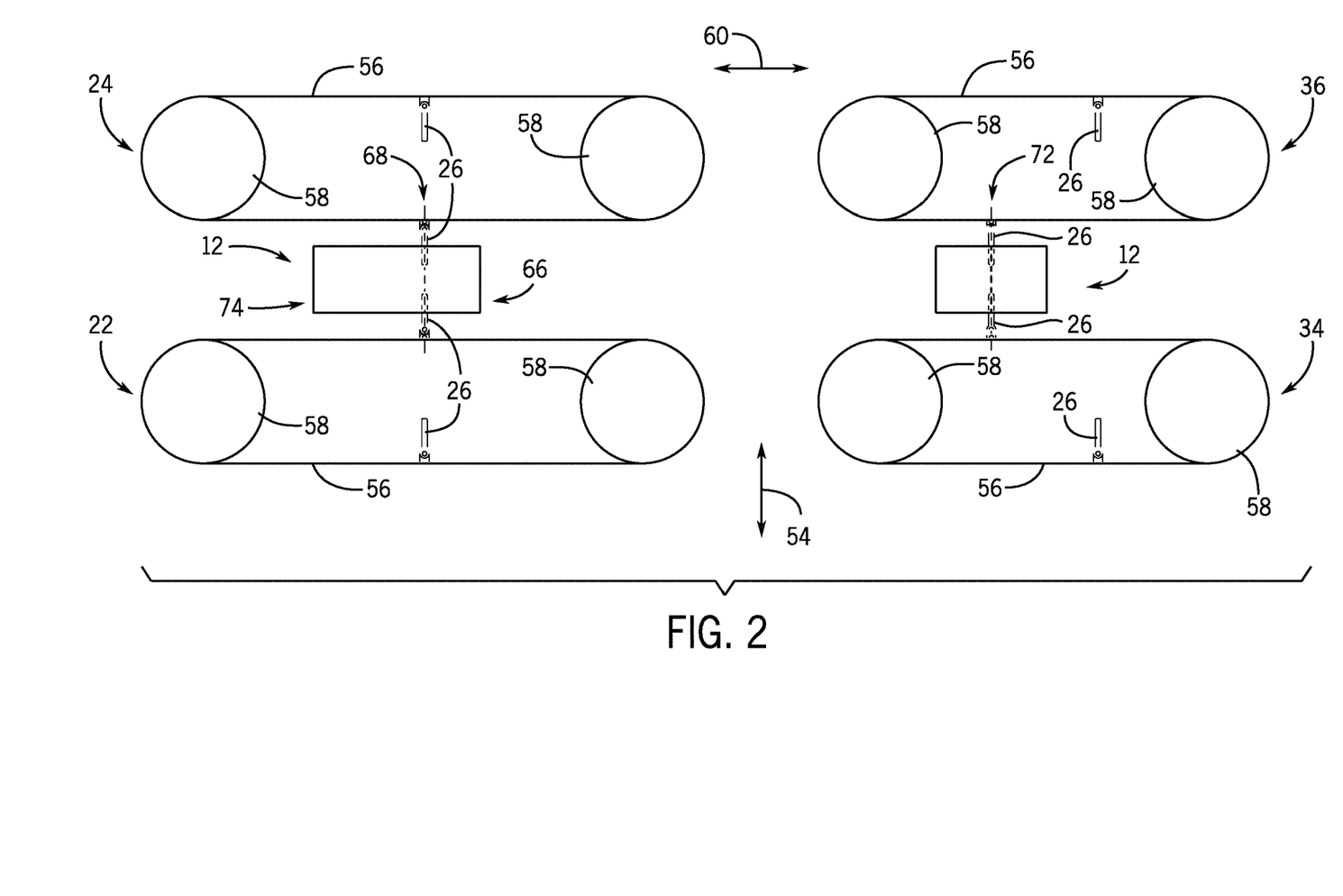
FIG. 2 is a top view of guide transporters and folding fingers portion included in the folding system of FIG. 1, according to an embodiment of the invention.

As article 12 begins to approach and engage a vacuum portion 42 of first vacuum drum 18, a folding finger 26 is controlled to approach the laid-out article 12 between main conveyor 14 and first vacuum drum 18. The folding finger 26 travels horizontally just below the bottom horizontal surface of conveyor 14 and below article 12 while oriented in a cross-machine direction. For simplicity of illustration, a single folding finger 26 is shown in FIG. 1, but in a preferred embodiment, two folding fingers 26 will cooperate in tandem to assist in folding of article 12, as shown in FIG. 2, with each folding finger 26 extending nearly roughly to a centerline of the article 12 in a cross-machine direction 54. It is noted that a single folding finger 26 could instead be used in the folding operation and that, in such an embodiment, only one guide transporter 22, 24 would be necessary.

Figure 4:
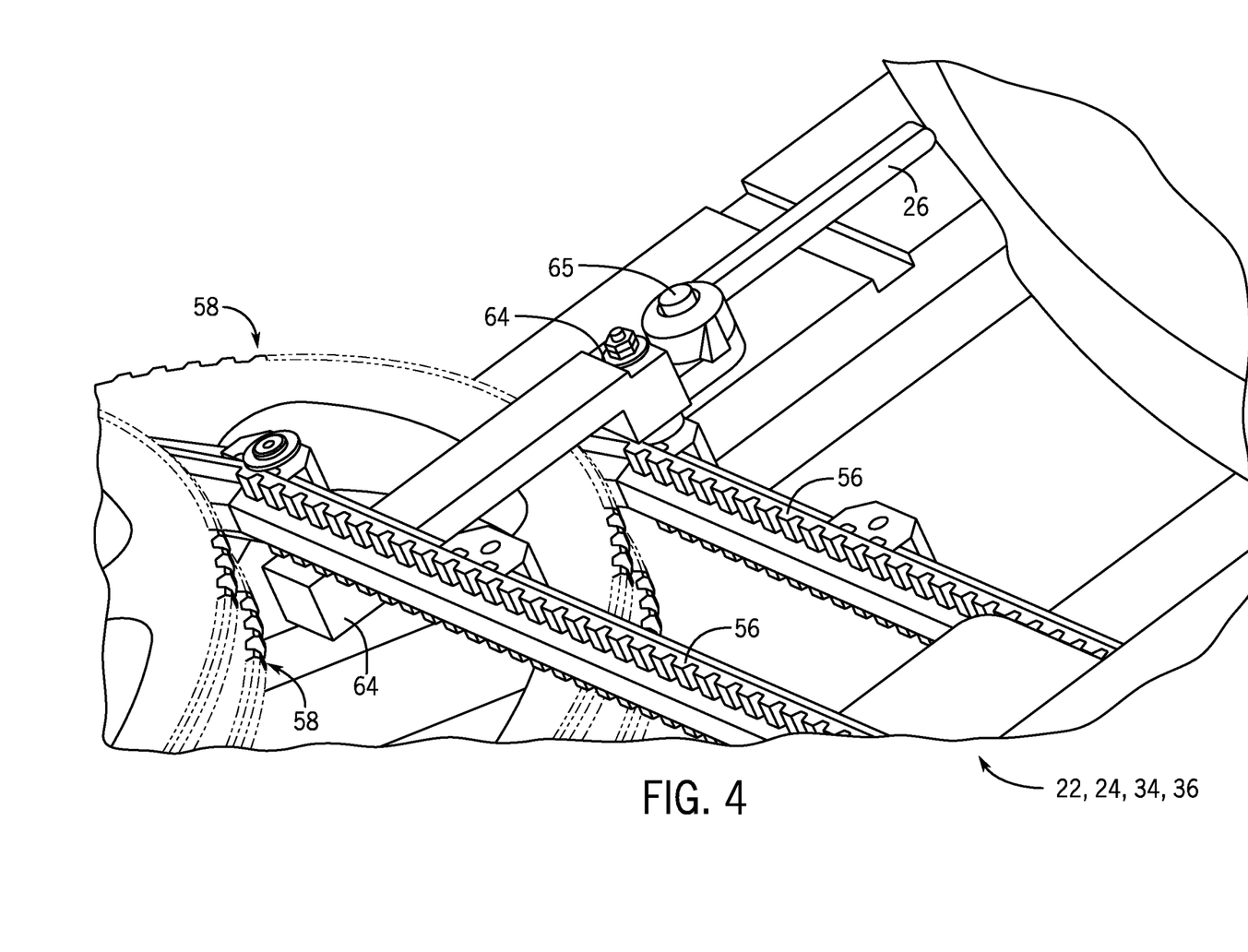
FIG. 4 is detailed perspective view of a portion of the guide transporters and folding fingers of FIG. 2, according to an embodiment of the invention.
Figure 5:
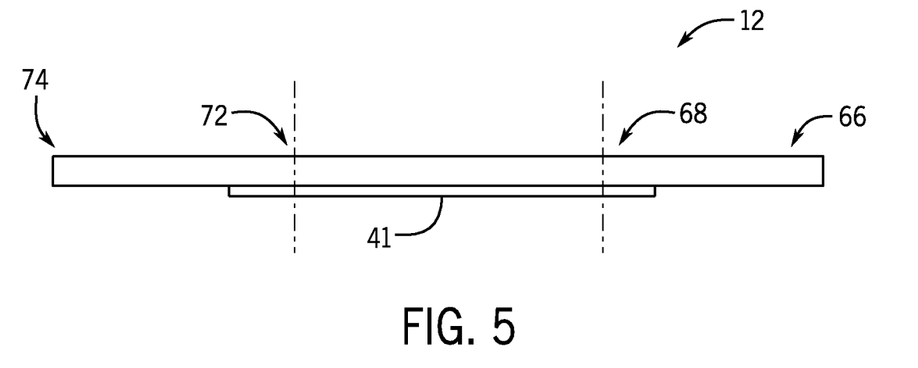
FIG. 5 is a side view of an absorbent sanitary product or article that may be folded at multiple locations by the folding system of FIG. 1.
Figure 6:
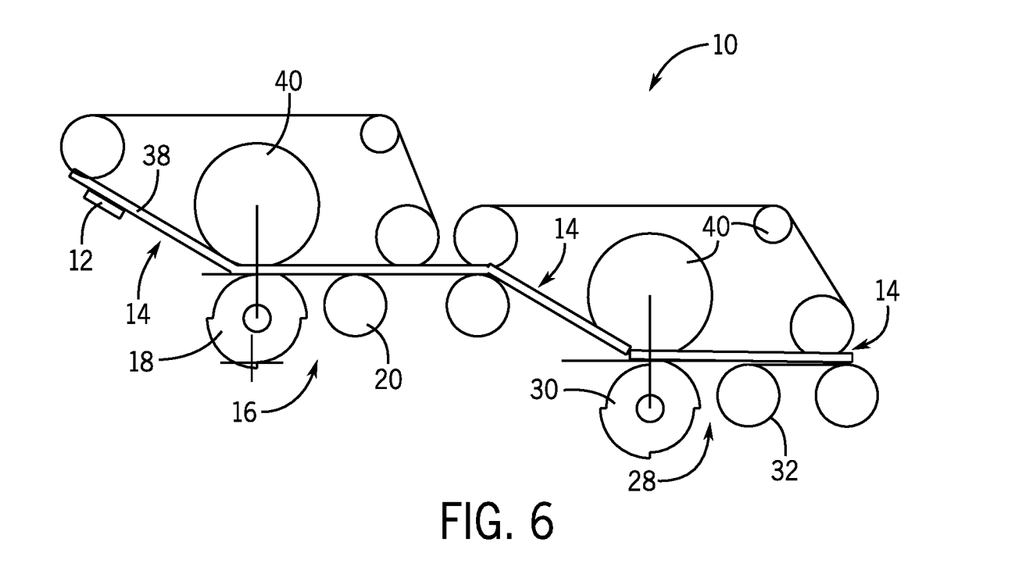
FIG. 6 is a schematic side view of a folding system for performing high-speed cross-folding of absorbent sanitary products or articles, according to an embodiment of the invention.

As best shown in FIGS. 1, 2, and 4, each of guide transporters 22, 24 (and guide transporters 34, 36) carry belts 56 that are rotated for instance by a servo motor and gear arrangement 58. The guide transporter(s) 22, 24 rotate (clockwise for transporter 22 and counterclockwise for transporter 24) to advance folding fingers 26 around the travel path of the belts 56. The guide transporter(s) 22, 24 are adapted to move the folding fingers 26 in a machine direction 60 (FIGS. 1 and 2) through a folding zone 62 in contact with the articles 12, with the folding fingers 26 maintained in the cross-machine direction when moving through the folding zone 62. The guide transporters 22, 24 may also move the folding fingers 26 in various other directions outside the folding zone 62 (and removing them from the path of the articles 12) as long as the folding fingers 26 are returned to the folding zone entrance and subsequently moved through the folding zone 62.

As shown in FIG. 4, folding fingers 26 are secured to both the belts 56 of guide transporter 22, 24 via a mount 64 that attaches the folding fingers 26 to both the belts 56. Because the mount 64 secures a folding finger 26 at two points to the two simultaneously rotating belts 56, the orientation of folding fingers 26 during travel with the belts 56 remains fixed in the cross-machine direction 54. The distance between the two belts 56 of the guide transporter 22, 24 remains constant. The belts 56 of each guide transporter 22, 24 are spaced apart from one another in the cross-machine direction 54 at a distance equal to the intended distance for cross-machine direction travel of folding fingers 26 during the folding sequence, with the diameter of the gears setting the distance of the cross-machine direction travel. Although two folding fingers 26 are shown carried by belts 56 of each of guide transporters 22, 24, more or less can be used according to preference.

According to one embodiment, each folding finger 26 is secured on its associated mount 64 via a pivot 65 that allows for rotation of the folding fingers 26 in the event of a malfunction of the folding system 10. For example, in the event of a jamming event or other malfunctioning of the folding system 10, folding fingers 26 may rotate about pivot 65 to be moved out of a path of the main conveyor 14 and drums 18, 20, 30, 32 of their associated folding station 16, 28 in order to prevent breaking/damage to the folding fingers 26 and/or damage to other components in the folding system 10.

As indicated above, operation of guide transporters 22, 24 is controlled by a servo motor and gear arrangement 58 that causes rotation of belts 56 and corresponding movement of folding fingers 26. According to an exemplary embodiment, the servo motor and gear arrangement 58 is controlled to match a speed of the belts 56 to the speed of main conveyor 14—such that folding fingers 26 move through the folding zone 62 at a same speed as articles 12. Additionally, the timing of positioning of folding fingers 26 on the belt 56 may be controlled so as to control a positioning of folding fingers 26 relative to articles 12, such that articles 12 may be folded at a desired location. The positioning of folding fingers 26 relative to each article 12 is maintained to provide a consistent folding location for each article 12 as it passes through first folding station 16.

As an article 12 advances through first folding station 16, a leading edge or portion 66 (FIG. 5) of the article 12 is picked up by rotating first vacuum drum 18 by vacuum ports 44 on vacuum portion 42, which are activated as previously described. The rotating first vacuum drum 18 carries the leading edge/portion 66 of article 12 further away from main conveyor 14, and folding fingers 26 approach a section or location 68 of article 12 that, according to an exemplary embodiment, is at a location off-center from the article 12 and more towards the leading edge of the article 12, as desired for performing the first fold. As folding finger 26 approaches closer to the desired location 68 of article 12, it is positioned proximate notched portion 48 of first vacuum drum 18, which allows for passage of the folding finger 26 past the first vacuum drum 18. The folding fingers 26 then contact article 12 at the desired location 68 to initiate a fold at the point of contact, while the leading edge/portion 66 of article 12 is still carried by rotating first vacuum drum 18.

At a pre-determined time, vacuum ports 44 on vacuum portion 42 of first vacuum drum 18 are deactivated, such that article 12 is released therefrom and caused to engage second vacuum drum 20 as it rotates in a clockwise direction—with second vacuum drum 20 engaging article 12 on a side thereof opposite absorbent insert 41. According to one embodiment, second vacuum drum 20 is configured as a vacuum drum with vacuum ports 44 thereon, so as to enhance engagement of article 12 to drum 20 after it is released from first vacuum drum 18, but it is recognized that second vacuum drum 20 need not be configured as a vacuum drum. Drums 18, 20 are closely spaced together to maintain control of article 12, with second vacuum drum 20 assisting the leading edge/portion 66 of article 12 upwards during rotation back towards main conveyor 14 to lay a leading part of the article 12 over a trailing part of the article 12. The clockwise rotational velocity of the outermost perimeter of second vacuum drum 20 is substantially equal to the speed of main conveyor 14, as well as substantially equal to the clockwise rotational velocity of the first vacuum drum 18 to avoid shear forces on article 12 and to establish a controlled laydown of the leading edge/portion 66 of folded article 12. Upon completion of the first fold at location 68, article 12 is released from second vacuum drum 20 and maintained on main conveyor 14 to move out of first folding station 16, with the article 12 being folded such that part of the article 12 is folded over on itself (two layers stacked on each other) but another part of the article 12 remains as a single layer.

While first folding station 16 is described above and illustrated in FIGS. 1 and 3 as including first and second drums 18, 20 to enable positioning and folding of the article in the manner described above, it is recognized that second drum 20 (and/or second drum 32 in second folding station 28) could be replaced by another type of suitable rotating member. For example, a belt that rotates in the clockwise direction could replace second drum 20 and operate in a likewise manner as that described above. The belt would thus engage article 12 (after engagement and release from first drum 18) on a side thereof opposite absorbent insert 41 and rotate the article 12 upwards back towards main conveyor 14 to lay a leading part of the article 12 over a trailing part of the article 12.

Upon completion of a folding operation at first folding station 16, the article 12 is translated along inverted main conveyor 14 toward second folding station 28. In moving toward second folding station 28, articles 12 are maintained in a folded state via a first compression conveyor 70 that is positioned adjacent and beneath main conveyor 14 between the first and second folding stations 16, 28. That is, articles 12 are sandwiched between the main conveyor 14 and first compression conveyor 70 as they move toward the second folding station 28, such that they are maintained in their folded state. As shown in FIG. 1, as main conveyor 14 approaches second folding station 28, the main conveyor 14 (and first compression conveyor 70) is oriented at a decline so as to assist folding fingers 26 at second folding station 28 in engaging the article 12 while it is moving on the conveyor 14.

As main conveyor 14 carries an article 12 to the second folding station 28, main conveyor 14 interacts with the first vacuum drum 30 of second folding station 28 that rotates/operates clockwise as shown in the view of FIG. 1 to transport the article 12. The first vacuum drum 30 may be identical in construction to first vacuum drum 18 at first folding station 16, and thus a detailed description of the vacuum drum 30 is not repeated here. However, it is recognized that first vacuum drum 30 may be reduced in size/diameter as compared to first vacuum drum 18, according to an embodiment of the invention. This reduction in size may be desirable to reduce an overall size/footprint of folding system 10 and is feasible based on the length of articles 12 being reduced as they enter the second folding station 28 (due to their being in a partially folded state).

As article 12 begins to approach and engage a vacuum portion 42 of first vacuum drum 30, a folding finger 26 is controlled to approach the laid-out article between main conveyor 14 and first vacuum drum 30. The folding finger 26 travels horizontally just below the bottom horizontal surface of conveyor 14 and below article 12 while oriented in a cross-machine direction 54. Again, while a single folding finger 26 is shown in FIG. 1, a preferred embodiment would include two folding fingers 26 that cooperate in tandem to assist in folding of article 12 (see FIG. 2)—with each folding finger 26 extending nearly roughly to a centerline of the article 12 in the cross-machine direction 54. As indicated above, positioning of folding fingers 26 relative to a lengthwise position of article 12 may be determined based on operation of guide transporters 34, 36, with the timing of positioning of folding fingers 26 on the belts 56 being controlled so as to control a positioning of folding fingers 26 relative to articles 12. At second folding station 28, the positioning of folding fingers 26 relative to each article 12 is controlled such that the folding fingers 26 are approach a second folding section or location 72 of article 12 that is at a location off-center from the article 12 and more towards the trailing edge/portion 74 of the article 12, as desired for performing the second fold. As folding finger 26 approaches closer to the second folding location 72 of article 12, it is positioned proximate notched portion 48 of the first vacuum drum 30, which allows for passage of the folding finger 26 past the first vacuum drum 30.

In interacting with first vacuum drum 30, the folded portion of article 12 is caused to engage the vacuum portion 42 of first vacuum drum 30 and become secured thereto. At a pre-determined time, vacuum ports 44 on vacuum portion 42 of first vacuum drum 30 are deactivated, such that article 12 is released therefrom and caused to engage second vacuum drum 32 as it rotates in a clockwise direction—with second vacuum drum 32 engaging article 12 on a side thereof opposite absorbent insert 41. Again, second vacuum drum 32 may be configured as a vacuum drum with vacuum ports 44 thereon, so as to enhance engagement of article 12 to second vacuum drum 32 after it is released from first vacuum drum 30, but it is recognized that second vacuum drum 32 need not be configured as a vacuum drum. Second vacuum drum 32 assists the folded portion of article 12 upwards during rotation back towards inverted main conveyor 14 to lay the folding part of the article 12 over a trailing (and previously unfolded) part of the article 12. The clockwise rotational velocity of the outermost perimeter of second vacuum drum 32 is substantially equal to the speed of main conveyor 14, as well as substantially equal to the clockwise rotational velocity of the first vacuum drum 30 to avoid shear forces on article 12 and to establish a controlled laydown of the leading part of folded article 12. Upon completion of the second fold, article 12 is released from second vacuum drum 32 and maintained on main conveyor 14 to move out of second folding station 28—with the article 12 being maintained in a folded state via a second compression conveyor 76 that is positioned adjacent and beneath main conveyor 14. The resulting folded article 12 is folded in thirds, with the folded article 12 having three layers of material.

Beneficially, embodiments of the invention thus provide an apparatus and method for performing high-speed crossfolding of feminine hygiene articles that will provide a desired folding pattern in the article. The apparatus and method may be incorporated into existing product manufacturing lines, without major modifications to the lines having to be made. Embodiments of the invention disclosed herein also provide a lower cost, more reliable system and method for folding such articles than existing systems and methods.

Therefore, according to one embodiment of the invention, a method for folding discrete absorbent sanitary products includes conveying an absorbent sanitary product in a machine direction along an inverted main conveyor and performing a first folding of the absorbent sanitary product at a first folding station, the first folding being performed at a first folding point of the absorbent sanitary product located between a leading edge and a midsection of the absorbent sanitary product. The method also includes performing a second folding of the absorbent sanitary product at a second folding station, the second folding being performed at a second folding point of the absorbent sanitary product located between a trailing edge and a midsection of the absorbent sanitary product. In performing each of the first folding and the second folding at the first folding station and the second folding station, respectively, the method further includes engaging the absorbent sanitary product with a first drum and rotating the absorbent sanitary product in a first rotational direction, contacting the absorbent sanitary product with one or more folding fingers traveling in the machine direction, engaging the absorbent sanitary product with a second drum adjacent to the first drum and downstream therefrom in the machine direction, the second drum rotating in the first rotational direction, and folding the absorbent sanitary product over the one or more folding fingers via rotation of the second drum in the first rotational direction.

According to another embodiment of the invention, a folding system for folding a plurality of discrete absorbent sanitary products includes an inverted main conveyor configured to convey absorbent sanitary products thereon in a machine direction, the absorbent sanitary products being maintained on the main conveyor via a vacuum, a first folding station positioned to receive the absorbent sanitary products on the main conveyor and controlled to perform a first folding thereof at a first folding point between a leading edge and a midsection of the absorbent sanitary product, and a second folding station positioned downstream from the first folding station in the machine direction to receive the absorbent sanitary products on the main conveyor after the first folding thereof, the second folding station controlled to perform a second folding thereof at a second folding point between a trailing edge and a midsection of the absorbent sanitary product. Each of the first folding station and the second folding station further includes a first drum rotating in the machine direction to engage an absorbent sanitary product and cause the leading edge of the absorbent sanitary product to rotate away from the main conveyor, a second drum positioned adjacent the first drum and downstream in the machine direction, the second drum rotating in the machine direction to engage the absorbent sanitary product and cause the absorbent sanitary product to rotate back toward the main conveyor, and one or more guide transporters each comprising a plurality of folding fingers, with each of the one or more guide transporters configured to translate a folding finger of the plurality of folding fingers in the machine direction at a same speed as the main conveyor and position the folding finger to contact the absorbent sanitary product. The absorbent sanitary product is folded over the folding finger as the second drum causes the absorbent sanitary product to rotate back toward the main conveyor.

According to yet another embodiment of the invention, a method of assembling a folding system includes providing an inverted main conveyor configured to convey absorbent sanitary products thereon in a machine direction, the absorbent sanitary products being maintained on the main conveyor via a vacuum, positioning a first folding station at a first location on the main conveyor to receive the absorbent sanitary products, the first folding station controlled to perform a first folding thereof at a first folding point between a leading edge and a midsection of the absorbent sanitary product, and positioning a second folding station at a second location on the main conveyor downstream from the first location to receive the absorbent sanitary products after the first folding thereof, the second folding station controlled to perform a second folding thereof at a second folding point between a trailing edge and a midsection of the absorbent sanitary product. In positioning each of the first folding station and the second folding station, the method further includes providing a first drum that rotates in the machine direction to engage an absorbent sanitary product and cause the leading edge of the absorbent sanitary product to rotate away from the main conveyor, providing a second drum positioned adjacent the first drum and downstream in the machine direction that rotates in the machine direction to engage the absorbent sanitary product and cause the absorbent sanitary product to rotate back toward the main conveyor, and providing one or more guide transporters that each comprises a plurality of folding fingers, with each of the one or more guide transporters configured to translate a folding finger of the plurality of folding fingers in the machine direction at a same speed as the main conveyor and position the folding finger to contact the absorbent sanitary product, so as to provide for folding of the absorbent sanitary product over the folding finger as the second drum causes the absorbent sanitary product to rotate back toward the main conveyor.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed is:

1. A method for folding discrete absorbent sanitary products, the method comprising:
   providing a first folding station;
   providing a second folding station downstream from the first folding station;
   providing a belt-type inverted main conveyor configured to transport discrete absorbent sanitary products at a constant speed in a machine direction across each of the first and second folding stations, the sanitary products to be folded at the first and second folding stations;
   providing a sloping compression conveyor between the first folding station and the second folding station, the sloping compression conveyor positioned beneath the inverted main conveyor;
   the sloping compression conveyor sloping in a downward direction from the first folding station toward the second folding station;
   conveying, by the inverted main conveyor, an absorbent sanitary product in a pad-down inverted orientation in a machine direction along the inverted main conveyor;
   performing a first folding of the absorbent sanitary product at the first folding station, the first folding occurring at a first folding location of the absorbent sanitary product located between a leading edge and a midsection of the absorbent sanitary product;
   the sloping compression conveyor configured to receive the folded absorbent sanitary product from the first folding station and maintain the absorbent sanitary product in a folded state against the inverted main conveyor;
   performing a second folding of the absorbent sanitary product at the second folding station, the second folding occurring at a second folding location of the absorbent sanitary product located between a midsection and a trailing edge of the absorbent sanitary product;

wherein performing each of the first folding and the second folding at the respective folding stations further comprises:

engaging the absorbent sanitary product with a first drum and rotating the absorbent sanitary product in a first rotational direction;

contacting the absorbent sanitary product with one or more folding fingers traveling in the machine direction, and traveling at a same speed as the inverted main conveyor;

engaging the absorbent sanitary product with a rotating member adjacent to the first drum and downstream therefrom in the machine direction, the rotating member rotating in the first rotational direction; and folding the absorbent sanitary product over the one or more folding fingers via rotation of the rotating member in the first rotational direction.

2. The method of claim 1 wherein conveying the absorbent sanitary comprises conveying the absorbent sanitary product along the inverted main conveyor in a pad down orientation, such that a first side of the absorbent sanitary product that includes an absorbent pad thereon faces away from the inverted main conveyor.

3. The method of claim 2 wherein the rotating member comprises a second drum, and wherein engaging the absorbent sanitary product with the first and second drums at the first folding station comprises:

engaging the first side of the absorbent sanitary product with the first drum to cause the leading edge of the absorbent sanitary product to rotate further away from the inverted main conveyor;

releasing the absorbent sanitary product from the first drum; and engaging a second side of the absorbent sanitary product with the second drum to cause the absorbent sanitary product to rotate back towards the inverted main conveyor.

4. The method of claim 3 wherein engaging the first side of the absorbent sanitary product with the first drum comprises activating a vacuum portion of the first drum to cause the absorbent sanitary product to engage the first drum.

5. The method of claim 4 wherein the vacuum portion juts out in a radial direction from a non-vacuum portion of the first drum, and wherein notches in the first drum are positioned at points where the vacuum portion transitions to the non-vacuum portion.

6. The method of claim 5 further comprising positioning the one or more folding fingers proximate a respective notch of the notches when the one or more folding fingers engage the absorbent sanitary product, so as to allow for passage of the one or more folding fingers past the first drum.

7. The method of claim 2 wherein the inverted main conveyor is sloped downward at locations feeding into the first folding station and the second folding station.

8. The method of claim 1 wherein performing the first and second foldings of the absorbent sanitary product folds the absorbent sanitary product into thirds.

9. The method of claim 1 further comprising controlling the one or more folding fingers to move into a folding zone to contact the absorbent sanitary product and move out of the folding zone and out of a path of the absorbent sanitary product, wherein controlling the one or more folding fingers comprises advancing the one or more folding fingers around a travel path of a pair of belts to which each of the one or more folding fingers are mounted, as part of one or more guide transporters.

10. The method of claim 9 wherein the one or more guide transporters are controlled to position the one or more folding fingers of each of the first and second folding stations at the first folding location and the second folding location, respectively.

11. A folding system for folding a plurality of discrete absorbent sanitary products, the folding system comprising:

a first folding station;

a second folding station downstream from the first folding station;

a belt-type inverted main conveyor configured to transport discrete absorbent sanitary products at a constant speed in a machine direction across each of the first and second folding stations, the sanitary products to be folded at the first and second folding stations;

a sloping compression conveyor located between the first folding station and the second folding station, the sloping compression conveyor positioned adjacent and beneath the inverted main conveyor, and sloping in a downward direction;

the inverted main conveyor configured to convey absorbent sanitary products thereon in a machine direction, the absorbent sanitary products being maintained in a pad-down orientation on the inverted main conveyor via a vacuum;

the first folding station operatively positioned to receive the absorbent sanitary products from the inverted main conveyor and controlled to perform a first folding thereof at a first folding location on the absorbent sanitary product between a leading edge and a midsection of the absorbent sanitary product;

the second folding station configured to receive the absorbent sanitary after the first folding thereof, the second folding station controlled to perform a second folding thereof at a second folding location on the absorbent sanitary product between a trailing edge and a midsection of the absorbent sanitary product;

the sloping compression conveyor configured to receive the folded absorbent sanitary product from the first folding station, and maintain the absorbent sanitary product in a folded state against the inverted main conveyor;

wherein each of the first folding station and the second folding station comprises:

a first drum rotating in the machine direction to engage an absorbent sanitary product and cause the leading edge of the absorbent sanitary product to rotate away from the inverted main conveyor;

a rotating member positioned adjacent the first drum and downstream in the machine direction, the rotating member rotating in the machine direction to engage the absorbent sanitary product and cause the absorbent sanitary product to rotate back toward the inverted main conveyor;

one or more guide transporters each comprising a plurality of folding fingers, with each of the one or more guide transporters configured to translate a folding finger of the plurality of folding fingers in the machine direction at a same speed as the inverted main conveyor and position the folding finger to contact the absorbent sanitary product; and wherein the absorbent sanitary product is folded over the folding finger as the rotating member causes the absorbent sanitary product to rotate back toward the inverted main conveyor.

12. The folding system of claim 11 wherein the one or more guide transporters in each of the first and second folding stations position the respective folding finger to cause the absorbent sanitary product to fold at the first folding location and the second folding location, respectively, so as to fold the absorbent sanitary product into thirds.

13. The folding system of claim 11 wherein each of the one or more guide transporters further comprises:
   a servo motor; and
   a pair of belts coupled to the servo-motor so as to be driven thereby to rotate around a travel path;
   wherein the plurality of folding fingers is mounted to the pair of belts to rotate therewith, with the plurality of fingers being maintained in a cross-machine direction when translated in the machine direction.

14. The folding system of claim 13 wherein each of the plurality of folding fingers is mounted via a pivot that allows for rotation of the folding finger from the cross-machine direction upon a jamming of the folding finger.

15. The folding system of claim 11 wherein the first drum in each of the first and second folding stations comprises a vacuum drum including:
   one or more vacuum portions each including vacuum ports therein, the one or more vacuum portions each configured to selectively activate and de-activate formation of a vacuum to engage and release the absorbent sanitary product; and
   one or more non-vacuum portions separate from the one or more vacuum portions.

16. The folding system of claim 15 wherein a radius of the first drum at the one or more vacuum portions is greater than a radius of the first drum at the one or more non-vacuum portions, with a notch formed in the first drum at transitions between the one or more vacuum portions and the one or more non-vacuum portions.

17. The folding system of claim 16 wherein the folding finger is positioned proximate the notch as the absorbent sanitary product engages the first drum, so as to allow for passage of the folding finger past the first drum.

18. The folding system of claim 11 wherein the inverted main conveyor is sloped downward at locations feeding into the first folding station and the second folding station.

19. The folding system of claim 11 wherein the rotating member comprises a second drum having a diameter smaller than a diameter of the first drum.

20. The folding system of claim 11 wherein a size of the first drum in the second folding station is smaller than a size of the first drum in the first folding station and/or a size of the second drum in the second folding station is smaller than a size of the second drum in the first folding station.

21. A method of assembling a folding system, the method comprising:

providing a first folding station;
providing a second folding station downstream from the first folding station;
providing a main conveyor configured to transport absorbent sanitary products at a constant speed in a machine direction across each of the first and second folding stations;
providing a sloping compression conveyor between the first folding station and the second folding station, the compression conveyor positioned adjacent and beneath the main conveyor, and sloping in a downward direction from the first folding station toward the second folding station;
maintaining the absorbent sanitary products in a pad-down orientation on the main conveyor via a vacuum, and conveying the absorbent sanitary products in a machine direction;
controlling the first folding station to perform a first folding of the absorbent sanitary product at a first folding location between a leading edge and a midsection of the absorbent sanitary product;
the compression conveyor configured to receive the folded absorbent sanitary product from the first folding station and maintain absorbent sanitary product in a folded state against the main conveyor after the first folding, and provide the compressed folded absorbent sanitary product to the second folding station;
controlling the second folding station to perform a second folding of the absorbent sanitary product at a second folding location between a trailing edge and a midsection of the absorbent sanitary product;
wherein, during the first folding or second folding of the absorbent sanitary product, the method further comprises:
   providing a first drum that rotates in the machine direction to engage an absorbent sanitary product and cause the leading edge of the absorbent sanitary product to rotate away from the main conveyor;
   providing a second drum positioned adjacent the first drum and downstream in the machine direction that rotates in the machine direction to engage the absorbent sanitary product and cause the absorbent sanitary product to rotate back toward the main conveyor; and
   providing one or more guide transporters that each comprises a plurality of folding fingers, with each of the one or more guide transporters configured to translate a folding finger of the plurality of folding fingers in the machine direction at a same speed as the main conveyor and position the folding finger to contact the absorbent sanitary product, so as to provide for folding of the absorbent sanitary product over the folding finger as the second drum causes the absorbent sanitary product to rotate back toward the main conveyor.

* * * * *